(12) United States Patent
Hatta (10) Patent No.: US 10,426,447 B2
(45) Date of Patent: Oct. 1, 2019

(54) BIOPSY DEVICE

(71) Applicant: TERUMO KABUSHIKI KAISHA, Tokyo (JP)

(72) Inventor: Tomonori Hatta, Kanagawa (JP)

(73) Assignee: TERUMO KABUSHIKI KAISHA, Tokyo (JP)

( * ) Notice: Subject to any disclaimer, the term of this patent is extended or adjusted under 35 U.S.C. 154(b) by 738 days.

(21) Appl. No.: 14/671,517

(22) Filed: Mar. 27, 2015

(65) Prior Publication Data
US 2015/0196287 A1 Jul. 16, 2015

Related U.S. Application Data

(63) Continuation of application No. PCT/JP2013/073673, filed on Sep. 3, 2013.

(30) Foreign Application Priority Data

Sep. 27, 2012 (JP) .................................. 2012-214272

(51) Int. Cl.
*A61B 10/02* (2006.01)
(52) U.S. Cl.
CPC ................................ *A61B 10/0266* (2013.01)
(58) Field of Classification Search
CPC .......................... A61B 10/0266; A61B 10/0233
See application file for complete search history.

(56) References Cited

U.S. PATENT DOCUMENTS

| 2003/0114773 A1* | 6/2003 | Janssens ............ A61B 10/0233 600/564 |
| 2008/0058673 A1* | 3/2008 | Jansen ............... A61B 10/0266 600/567 |
| 2009/0112119 A1* | 4/2009 | Kim .................... A61B 10/0266 600/564 |
| 2010/0010492 A1* | 1/2010 | Lockard ............... A61B 17/221 606/79 |

(Continued)

FOREIGN PATENT DOCUMENTS

| JP | 2011-514905 A | 12/1999 |
| JP | 2010-502303 A | 1/2010 |

(Continued)

OTHER PUBLICATIONS

Japanese office action for Japanese patent application 2014-538322, dated Feb. 28, 2017, p. 2.

(Continued)

*Primary Examiner* — Sean P Dougherty
*Assistant Examiner* — Nicholas E Kolderman (57) ABSTRACT

Disclosed herein is a biopsy device for efficiently sampling a specimen from a biological tissue, particularly if the biological tissue is a soft tissue. The biopsy device includes: an elongate shaft; a piercing spike for piercing a biological tissue, the piercing spike being disposed on a longitudinally distal end of the elongate shaft; a screw disposed on the elongate shaft, for guiding a specimen sampled from a living body from the longitudinally distal end of the elongate shaft toward a longitudinally proximal end thereof; and a screw cutter disposed on the screw, for peeling the specimen off the living body. The screw cutter peels the specimen off the biological tissue while the piercing spike is piercing the biological tissue.

12 Claims, 5 Drawing Sheets

(56) References Cited

U.S. PATENT DOCUMENTS

2012/0191121 A1* 7/2012 Chen .................. A61B 10/0266
606/180

FOREIGN PATENT DOCUMENTS

| WO | WO 9716118 A1 * | 5/1997 | ........... A61B 10/025 |
| WO | WO 1997016118 A1 * | 5/1997 | ........... A61B 10/025 |
| WO | 2011/004776 A1 | 1/2011 | |

OTHER PUBLICATIONS

English abstract of JP2010-502303, dated Jan. 28, 2010, p. 1.
English abstract of JP11-514905, dated Dec. 21, 1999, p. 2.

* cited by examiner

BIOPSY DEVICE

CROSS-REFERENCE TO RELATED APPLICATIONS

This application is continuation of International Application No. PCT/JP2013/073673 with an international filing date of Sep. 3, 2013, which claims priority to Japanese National Patent Application No. JP2012-214272 filed on Sep. 27, 2012. The entire contents of each and every foregoing applications are incorporated herein by reference.

BACKGROUND

The present disclosure relates to a biopsy device for sampling a specimen from a biological tissue.

A biopsy is a process of sampling a specimen from a biological tissue of a lesion of a patient who may be suffering a disease such as cancer or the like and inspecting the sampled specimen. In the biopsy, an operator samples the specimen from the biological tissue while visually observing the affected area or sampled region through an endoscope. In order to make a conclusive diagnosis of a disease on the basis of a biopsy, it is preferable for the operator to diagnose as many biological tissues as possible for higher diagnostic accuracy. Generally, however, since the biopsy instrument includes forceps and a needle, it is difficult to sample an amount of tissue required for a diagnosis from the patient in a single piercing process. JP-T-2004-517706 discloses a device including a helical tissue receiving element and a severing element for severing a tissue in cooperation with an outer circumferential surface of the helical tissue receiving element for the purpose of efficiently sampling a specimen from a biological tissue.

The device disclosed in JP-T-2004-517706 may appear to allow the tissue receiving element to sample a large amount of tissue in one sampling action. However, since the tissue receiving element is slender and helical, it is not sufficiently rigid. Therefore, when an operator attempts to pierce a biological tissue to secure the device in position with respect to the biological tissue, the operator finds it difficult to quickly pierce the biological tissue with a piercing spike and firmly secure the piercing spike of the device in place. This problem manifests itself when the biological tissue to be pierced is a soft tissue such as a liver or a lung. Inasmuch as the piercing spike is not securely held in position, the piercing spike may be dislodged while the operator is attempting to sample a specimen, and hence the operator may be unable to sample a specimen efficiently.

SUMMARY

It is an intention of the present disclosure to provide a biopsy device for efficiently sampling a specimen from a biological tissue, particularly if the biological tissue is a soft tissue.

According to the present disclosure, there is provided a biopsy device including an elongate shaft, a piercing spike for piercing a biological tissue, the piercing spike being disposed on a longitudinally distal end of the elongate shaft, a screw disposed on the elongate shaft, for guiding a specimen sampled from a living body from the longitudinally distal end of the elongate shaft toward a longitudinally proximal end thereof, and a screw cutter disposed on the screw, for peeling the specimen off the living body. The screw cutter peels the specimen off the biological tissue while the piercing spike is piercing the biological tissue.

The above and other intentions, features, and advantages of the present disclosure will become more apparent from the following description when taken in conjunction with the accompanying drawings in which a preferred embodiment of the present disclosure is shown by way of illustrative example.

Additional features, advantages, and embodiments of the invention may be set forth or apparent from consideration of the following detailed description, drawings, and claims. Moreover, it is to be understood that both the foregoing summary of the invention and the following detailed description are exemplary and intended to provide further explanation without limiting the scope of the invention as claimed.

DETAILED DESCRIPTION OF THE PREFERRED EMBODIMENT

A biopsy device according to an embodiment of the present disclosure will be described in detail below with reference to the accompanying drawings. The description given below should not be interpreted as limiting the technical scopes and terms contained in the claims of the present application. The ratios of dimensions in the accompanying drawings are shown as exaggerated for illustrative purposes, and may be different from the actual ratios of dimensions.

The terms "distal" and "proximal" referred to herein mean a region closer to the pointed tip of a biopsy device and a region closer to the base end thereof that is remote from the pointed end, respectively.

Figure 1:
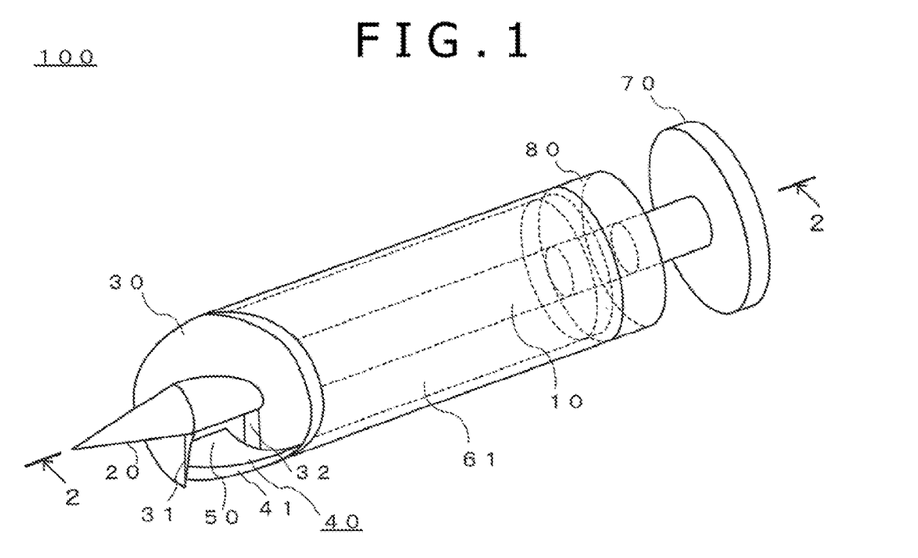
FIG. 1 is a perspective view of a biopsy device according to an embodiment of the present disclosure.
Figure 2:
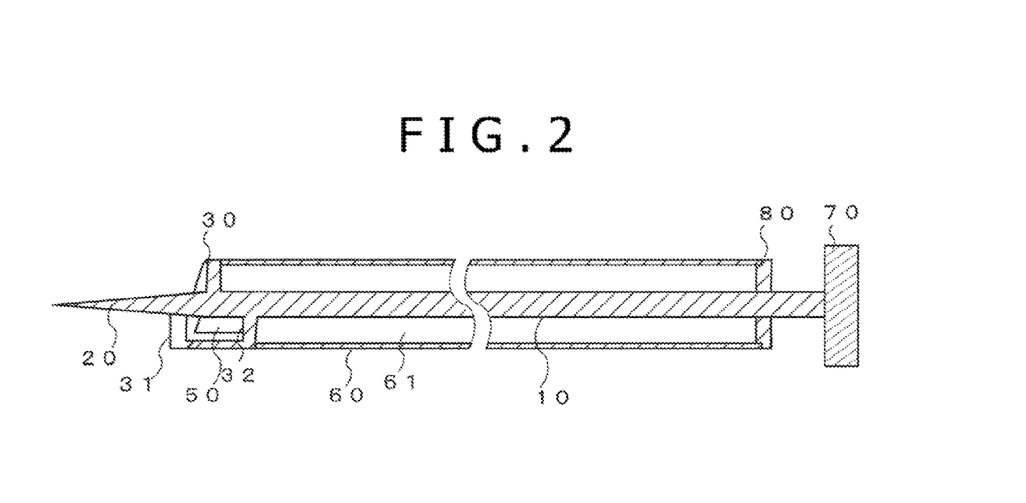
FIG. 2 is a cross-sectional view taken along line 2-2 of FIG. 1.
Figure 3:
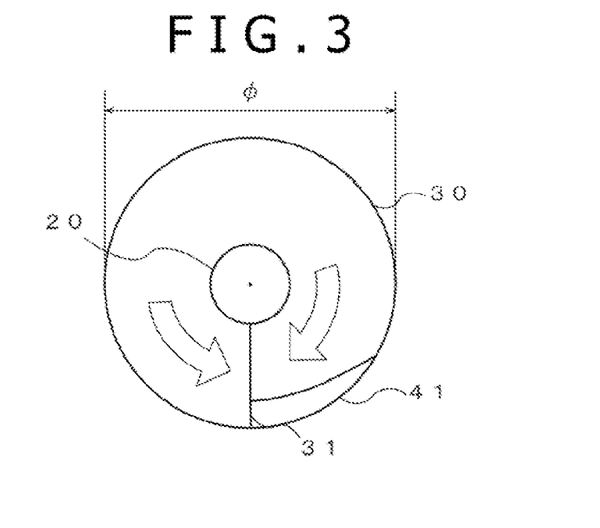
FIG. 3 is a front elevational view of the biopsy device.
Figure 4:
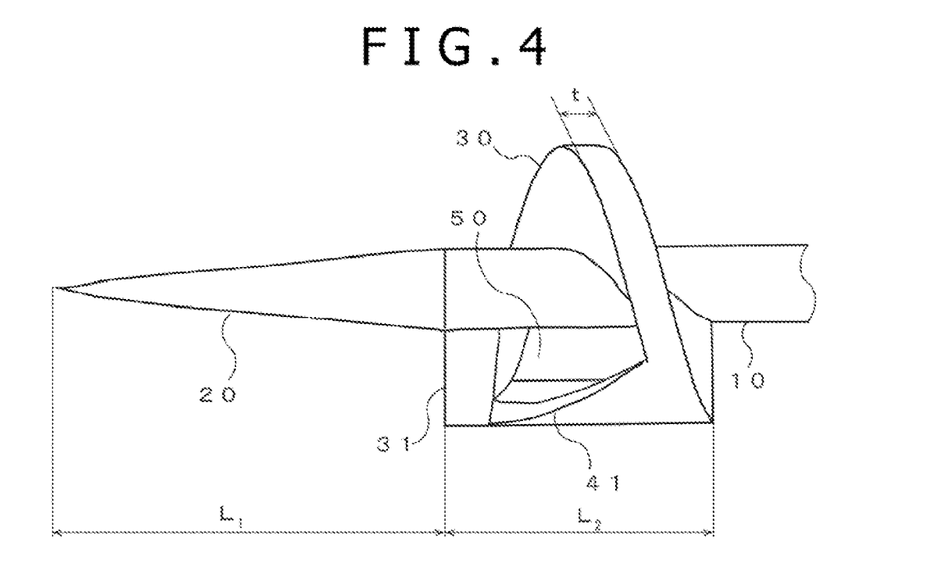
FIG. 4 is a right-hand side elevational view of the biopsy device.
Figure 5:
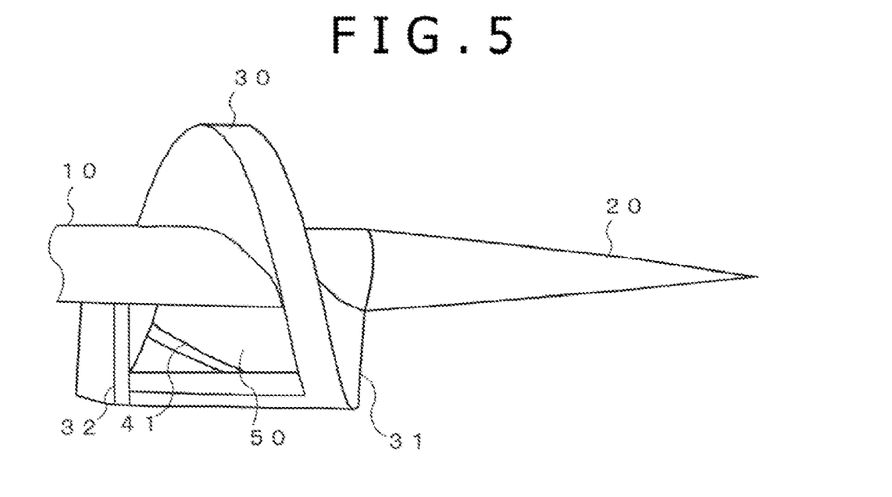
FIG. 5 is a left-hand side elevational view of the biopsy device.
Figure 6:
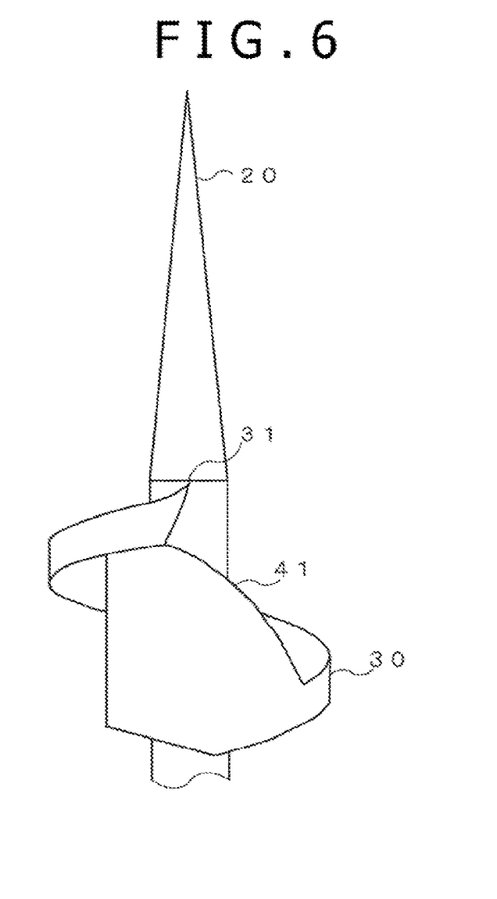
FIG. 6 is a bottom view of the biopsy device.

FIG. 1 shows in perspective a biopsy device according to an embodiment of the present disclosure. FIG. 2 is a cross-sectional view taken along line 2-2 of FIG. 1. FIG. 3 shows the biopsy device in front elevation, FIG. 4 shows the biopsy device in right-hand side elevation, FIG. 5 shows the biopsy device in left-hand side elevation, and FIG. 6 shows the biopsy device in bottom view.

As shown in FIGS. 1 through 6, a biopsy device 100 according to the embodiment of the present disclosure includes a shaft 10, a piercing spike 20 disposed on a longitudinally distal end of the shaft 10, and a helical screw 30 disposed on the shaft 10 closely to the piercing spike 20, for guiding a specimen to move from the distal end of the shaft 10 toward a longitudinally proximal end thereof. The biopsy device 100 also includes a first screw cutter 31 (corresponding to screw cutter) for peeling a specimen from a living body, the first screw cutter 31 being disposed on the screw 30 closely to the piercing spike 20, and a second screw cutter 32 (corresponding to other screw cutter) for separating the peeled-off specimen from the living body, the second screw cutter 32 being disposed on the screw 30 and axially spaced from the first screw cutter 31. The biopsy device 100 further includes a peripheral wall 40 extending continuously from the first screw cutter 31 toward the second screw cutter 32 and spaced radially outwardly from and covering a portion of the screw 30. The peripheral wall 40 has a blade 41 whose cutting edge is orientated in the same direction as the cutting edge of the first screw cutter 31. The first screw cutter 31, the second screw cutter 32, and the peripheral wall 40 jointly define therebetween an opening 50 for introducing therein the peeled specimen from the screw 30 toward the proximal end of the shaft 10. The shaft 10 is surrounded by a hollow tubular barrel 60 that is spaced radially outwardly from the shaft 10. A handle 70 and a holder 80 are disposed on the proximal end of the biopsy device 100. The handle 70 and the holder 80 will be described in detail below.

The handle 70, which is in the form of a cylindrical member coupled to the proximal end of the shaft 10, serves to rotate the shaft 10 and the screw 30. The handle 70 may have surface irregularities on its side surface for preventing itself from slipping when it is rotated. The handle 70 is preferably, but not necessarily, made of polypropylene, polycarbonate, or the like.

The holder 80 holds the shaft 10 rotatably in the tubular barrel 60. The holder 80 is fixed by thermal fusion or the like to the proximal end of the tubular barrel 60. The holder 80 may be made of the same material of the handle 70. However, the area of the holder 80 which is held in contact with the shaft 10 should preferably be made of wear-resistant plastics such as polycarbonate or the like in order that the contacting area of the holder 80 is prevented from reducing its retaining force due to wear.

The shaft 10 is in the form of an elongate member having on its distal end the piercing spike 20, the screw 30, and the peripheral wall 40. The shaft 10 should preferably be lightweight so that when the shaft 10 and the tubular barrel 60 are inserted into a complex organ such as the trachea leading to a lung, the shaft 10 will not have an impact on the organ even if it hits an inner surface of the organ. For sampling a specimen, the handle 70 is rotated to apply a torque to the shaft 10. Therefore, the shaft 10 is constructed to have a prescribed degree of torsional stiffness. The material, length, and cross-sectional shape of the shaft 10 are determined in order to meet such a requirement. For example, the shaft 10 may be made of Steel Use Stainless (SUS), may have a length of about 1000 mm, and may have a circular cross-sectional shape having a diameter of 0.4 mm. However, the shaft 10 is not limited to those material and dimensions.

The tubular barrel 60 is in the form of a hollow member whose proximal end is attached to the shaft 10 by the holder 80. The tubular barrel 60 surrounds the shaft 10 from the proximal end of the shaft 10 to the proximal end of the screw 30. A specimen that is sampled from a living body is introduced through the opening 50 into a lumen 61 of the tubular barrel 60. The lumen 61 is held in fluid communication with the opening 50 and is radially spaced from the living body by the tubular barrel 60. Specifically, the specimen that is sampled by the first screw cutter 31, the second screw cutter 32, and the blade 41 adheres to the screw 30 and the shaft 10 that extends from the screw 30 toward the proximal end of the tubular barrel 60. Since the specimen has a prescribed degree of viscosity, it adheres to the screw 30 and the shaft 10 and does not fall off the screw 30 and the shaft 10. Even if the specimen falls off the screw 30 and the shaft 10 at the time the biopsy device 100 is twisted or otherwise deformed, the specimen is prevented from being dislodged from the biopsy device 100 by the tubular barrel 60 that surrounds the shaft 10. Accordingly, the living body is protected against complications due to dissemination of the specimen which may contain malignant cells, for example.

A negative pressure generator such as a vacuum pump or the like may be connected to the proximal end of the tubular barrel 60. When the negative pressure generator thus connected to the tubular barrel 60 is actuated, a vacuum is developed in the tubular barrel 60, drawing a specimen sampled from a living body at the distal end of the biopsy device 100 through the opening 50 into the tubular barrel 60 and then out of the tubular barrel 60. The specimen can be taken out of the biopsy device 100 without being moved along the shaft 10 toward the proximal end thereof upon rotation of the shaft 10, pulling the biopsy device 100 out of the living body, and detaching the tubular barrel 60 from the shaft 10. Therefore, the specimen can efficiently be removed from the living body.

The piercing spike 20 serves to secure the biopsy device 100 in a living body from which to sample a specimen. The material and shape of the piercing spike 20 are determined in view of various factors including the ease with which the piercing spike 20 pierces a biological tissue, the difficulty with which the piercing spike 20 comes off a biological tissue after having pierced it, etc. Though the piercing spike 20 is shown as a pointed needle in the embodiment, the piercing spike 20 may be of, though not limited to, a spiral shape similar to the shape of a cork screw, a drill bit shape, or a saw-tooth shape to make itself easier to pierce a biological tissue. The piercing spike 20, which may have an axial length $L_1$ of 2 mm, for example, is relatively short so that it can be manipulated well when the biopsy device 100 is inserted in a complexly shaped tube such as a tube in a lung.

The piercing spike 20 may be inserted in a living body while the piercing spike 20 is being frozen to a temperature of about 0 degree, for example. When the piercing spike 20 thus frozen is inserted into a biological tissue, it freezes water around cells to be sampled from the biological tissue by the biopsy device 100, causing those cells to adhere easily to the piercing spike 20. Therefore, the piercing spike 20 is firmly secured in place by the biological tissue.

The helical screw 30 serves to guide a sampled specimen from the distal end of the biopsy device 100 toward the proximal end thereof. Specifically, the biopsy device 100 rotates about its own axis to deliver the sampled specimen from the distal end of the biopsy device 100 toward the proximal end thereof along the helical screw 30 and the shaft 10. The screw 30 may have its surface roughened or processed into a sticky surface for causing the sampled specimen to move smoothly therealong without dropping off the screw 30.

The screw 30 is made of stainless steel, for example. As shown in FIG. 4, the screw 30 has a wall thickness t of 0.2 mm, an axial length $L_2$ of 2 mm, and a diameter φ of 1.5 mm, as viewed in front elevation in FIG. 3, for example. However, the screw 30 is not limited to those material and dimensions.

The first screw cutter 31 serves to peel cells off a living body when the helical screw 30 is rotated counterclockwise about its own axis as viewed in front elevation in FIG. 3. Specifically, when rotated counterclockwise, the first screw cutter 31 severs cells of the living body in the vicinity thereof into a group of cells on a distal side of the first screw cutter 31 and a group of cells on a proximal side thereof, and peels the cells on the proximal side off the living body. In FIG. 3, the first screw cutter 31 is illustrated as extending along the radius of a circular shape onto which the helical screw 30 is projected as viewed in front elevation. However, the first screw cutter 31 may be of, though not limited to, a straight blade shape or a saw-tooth shape, for example.

The peripheral wall 40 is contiguous to the first screw cutter 31 and has an end joined to the screw 30. The peripheral wall 40 is spaced radially outwardly from and covers a portion of the screw 30. The peripheral wall 40 may be made of the same material as the screw 30 or may be made of a plastic material such as silicone or the like so that the peripheral wall 40 is pliable.

The blade 41 serves to peel cells positioned in the vicinity thereof off a living body when the first screw cutter 31 is rotated counterclockwise in FIG. 3. Specifically, the blade 41, which, is positioned on an outer circumferential surface of the screw 30, divides the cells in the vicinity thereof into a group of cells positioned radially inwardly of the blade 41 and a group of cells positioned radially outwardly of the blade 41, and peels the cells positioned radially inwardly of the blade 41 off the living body. The cutting edge of the blade 41 does not extend parallel to the axis of the shaft 10, but is curved such that when a point on the cutting edge moves from the distal end toward the proximal end of the cutting edge, the point is observed as moving along the outer profile of the screw 30 as viewed in front elevation in FIG. 3.

When the screw 30 starts to be rotated in a biological tissue to sample a specimen therefrom, the blade 41 thus shaped is initially brought into partial contact with the biological tissue from a proximal region of the blade 41, and then progressively cuts cells off the biological tissue. Therefore, the resistance that is imposed on the blade 41 upon contact with the biological tissue is reduced. The blade 41 is effective to reduce the number of occasions wherein a specimen cannot be severed from a biological tissue.

The second screw cutter 32 serves to separate cells that have been peeled off a living body by the first screw cutter 31, from the living body, when the screw 30 is rotated clockwise in FIG. 3. Specifically, the second screw cutter 32 separates cells that have been peeled from a living body by the first screw cutter 31 and the blade 41 into a group of cells on a distal side of the second screw cutter 32 and a group of cells on a proximal side thereof, and separates the cells on the proximal side as a specimen from the living body. The second screw cutter 32 separates cells from the cells peeled off the living body by the first screw cutter 31 and the blade 41, as a specimen from the living body, when the second screw cutter 32 is rotated in a direction opposite to the direction in which the first screw cutter 31 and the blade 41 were rotated to peel the cells. Consequently, the specimen can be sampled from the living body by a simple action.

Each of the first screw cutter 31, the second screw cutter 32, and the blade 41 has its cutting edge oriented at 45 degrees, for example, with respect to the rest thereof. However, the cutting edge of each of the first screw cutter 31, the second screw cutter 32, and the blade 41 may be oriented at different angles.

The specimen may be separated from the living body not only by rotating the biopsy device 100 but also by pulling the biopsy device 100 away from the living body toward the proximal side. The latter process also allows the specimen to be sampled from the living body through a simple action.

The opening 50 is defined jointly between the first screw cutter 31, the second screw cutter 32, and the peripheral wall 40. The cells peeled off the living body pass through the opening 50. The screw 30 and the peripheral wall 40 attached thereto guide the cells sampled by the first screw cutter 31 and the blade 41 to move only through the opening 50 toward the proximal end of the biopsy device 100. The screw 30 and the peripheral wall 40 are effective to prevent the sampled cells from being scattered around. Since the screw 30 and the peripheral wall 40 restrict the cells against moving in unwanted directions, the living body is protected against complications due to dissemination of malignant cells, for example.

The opening 50 may have a size of 1 mm×0.5 mm, for example. However, the opening 50 may be of other sizes.

A procedure for sampling a specimen from the living body of a patient using the biopsy device 100 according to the present embodiment will be described below with reference to FIGS. 7 through 9. It is assumed that the biopsy device 100 will be introduced into the patient's body to sample a specimen therefrom.

Before the biopsy device 100 is introduced into the patient's body, a route through which the biopsy device 100 is to be introduced can be confirmed by a medical image-capturing apparatus such as an X-ray apparatus, a Computed Tomography (CT) apparatus, or the like. Then, local anesthesia is given to the pharynx or larynx of the patient. The biopsy device 100 is introduced through the throat to a desired position of the patient while images of regions in the patient's body are being captured by the medical image-capturing apparatus. Alternatively, the biopsy device 100 may be introduced into the patient's body through the channel in a bronchoscope inserted into the patient's body.

The biopsy device 100 has been connected at its proximal end to a rotational force generator, not shown, for rotating the screw 30. While the biopsy device 100 is being introduced into the patient's body, the piercing spike 20 and the screw 30 are housed in the tubular barrel 60 for preventing themselves from scraping off tissues and causing pneumothorax or bleeding.

Figure 7:
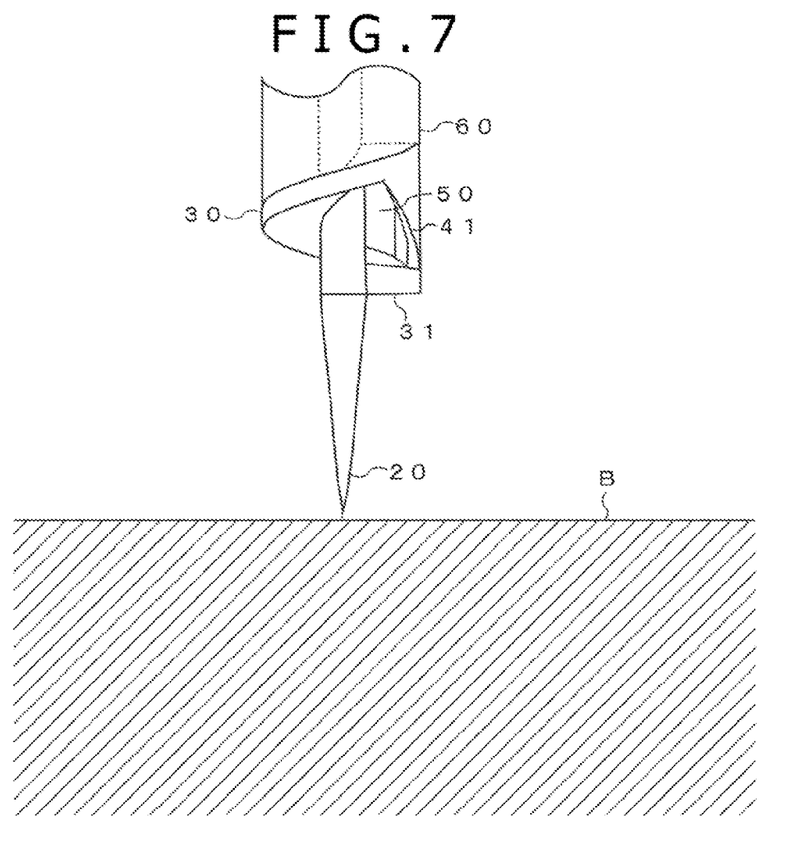
FIG. 7 is a view illustrating a procedure for sampling a specimen from a biological tissue with the biopsy device.
Figure 8:
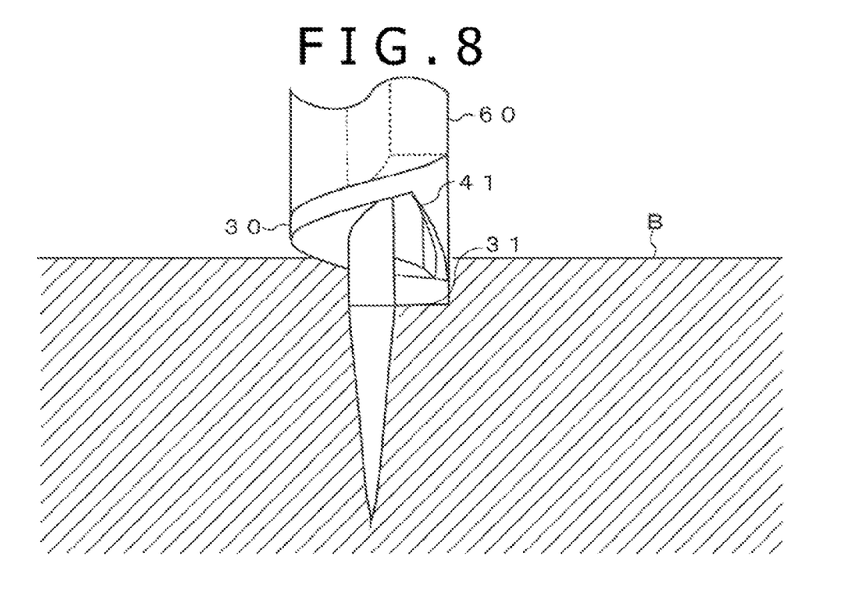
FIG. 8 is a view illustrating the procedure for sampling the specimen from the biological tissue with the biopsy device.

When the biopsy device 100 has reached the desired position as shown in FIG. 7, the piercing spike 20 and the screw 30 are projected from the tubular barrel 60. Then, as shown in FIG. 8, the piercing spike 20 is pushed on to pierce a biological tissue B, securing the biopsy device 100 to the living body. Thereafter, the rotational force generator is energized to rotate the screw 30 counterclockwise in FIG. 3.

Figure 9:
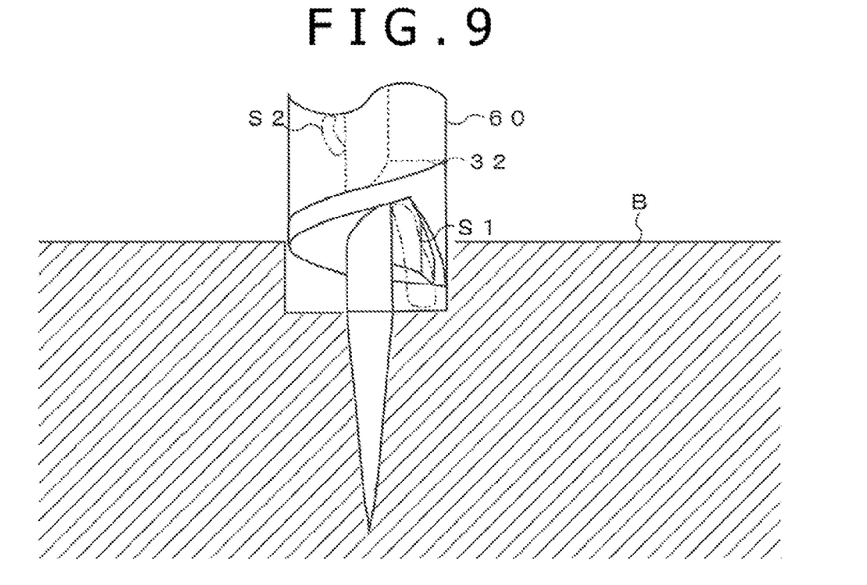
FIG. 9 is a view illustrating the procedure for sampling the specimen from the biological tissue with the biopsy device.

The first screw cutter 31, as shown in FIG. 9, which is positioned on the distal end of the helical screw 30, severs cells of the biological tissue B in the vicinity thereof into a group of cells on the distal side of the first screw cutter 31 and a group of cells on the proximal side thereof. The cells, which are denoted by S1 and S2 in FIG. 9, on the proximal side are peeled off biological tissue B and guided into the opening 50. Similarly, the blade 41 of the peripheral wall 40 divides the cells in the vicinity thereof into a group of cells positioned radially inwardly of the blade 41 and a group of cells positioned radially outwardly of the blade 41. The cells S1 and S2 that are positioned radially inwardly of the blade 41 are guided into the opening 50.

Upon rotation of the shaft 10, the cells S1 and S2 are guided from the opening 50 along the shaft 10 toward the proximal end of the biopsy device 100.

When a necessary amount of cells has been peeled off, the rotational force generator is de-energized, and energized again to rotate the screw 30 clockwise in FIG. 3. The cells S1 and S2 peeled off the biological tissue B are now separated into a group of cells on the distal side of the second screw cutter 32 and a group of cells on the proximal side thereof. The cells S1 and S2 on the proximal side are separated as a specimen from the biological tissue B. After the cells S1 and S2 separated as the specimen have been introduced into the tubular barrel 60, the rotational force generator is de-energized, and the piercing spike 20 is pulled out of the patient's body. The piercing spike 20 and the screw 30 are retracted back into the tubular barrel 60, and the biopsy device 100 is removed from the patient's body.

Some biopsy devices sample a specimen from a biological tissue when a screw-shaped member thereof is rotated. If the biopsy device and the biological tissue are sufficiently secured to each other, then the biological tissue tends to rotate with the biopsy device when the biopsy device is rotated. If the biological tissue rotates with the biopsy device, then the biopsy device is unable to peel and sample cells from the biological tissue. This problem manifests itself when the biological tissue to be pierced is a soft tissue such as a liver or a lung. Furthermore, if the biopsy device and the living body are not quickly secured to each other, then the sampling of a specimen is delayed, and hence a specimen cannot efficiently be sampled from the biological tissue.

The biopsy device 100 according to the present embodiment operates by causing the piercing spike 20 on the distal end of the shaft 10 to pierce the biological tissue B, thereby securing the biopsy device 100 to the biological tissue B, and then peeling off and sampling a specimen from the living body with the first screw cutter 31 of the screw 30 on the shaft 10. When the specimen is peeled off the living body by the first screw cutter 31, the biopsy device 100 is firmly secured to the living body by the piercing spike 20 on the shaft 10. The biopsy device 100 cannot easily be dislodged from the living body when the screw 30 is rotated to sample the specimen from the living body. Consequently, the specimen can easily be peeled off and efficiently sampled from the biological tissue B even if the biological tissue B is a soft tissue.

As described above, the biopsy device 100 according to the present embodiment includes the elongate shaft 10, the piercing spike 20 for piercing the biological tissue B, the piercing spike 20 being disposed on a longitudinally distal end of the shaft 10, the helical screw 30 disposed on the shaft 10, for guiding a specimen sampled from the biological tissue B to move from the distal end of the shaft 10 toward a longitudinally proximal end thereof, and the first screw cuter 31 on the screw 30, for peeling cells off the living body. The first screw cutter 31 peels the cells off the biological tissue B while the piercing spike 20 is piercing the biological tissue B.

Consequently, the biopsy device 100 is capable of quickly sampling a specimen from the living body while it is being firmly secured to the living body. The biopsy device 100 is thus able to sample the specimen efficiently from the biological tissue B even if the biological tissue B is a soft tissue.

The screw 30 also has, in addition to the first screw cutter 31, the second screw cutter 32 for separating a desired amount of cells among the cells peeled off the living body from the living body. Therefore, the cells peeled off the living body can be separated as a specimen from the living body. The biopsy device 100 prevents more than necessary cells from being sampled from the living body, and can quickly sample the specimen from the living body.

The first screw cutter 31 is disposed on the distal end of the screw 30, and the biopsy device 100 includes the peripheral wall 40 extending continuously from the first screw cutter 31 toward the second screw cutter 32 and spaced radially outwardly from and covering a portion of the screw 30. The peripheral wall 40 is effective to prevent the cells peeled off the living body by the first screw cutter 31 from being scattered outwardly from the screw 30, thereby protecting the living body against complications due to dissemination of malignant cells, for example.

The opening 50 for receiving the sample therein is defined jointly between the first screw cutter 31, the second screw cutter 32, and the peripheral wall 40. The specimen peeled off by the first screw cutter 31 and the blade 41 and separated by the second screw cutter 32 is guided to move only through the opening 50 so as to be sampled by the biopsy device 100. The first screw cutter 31 and the second screw cutter 32 are effective to prevent the sampled cells from being scattered around in longitudinal directions of the biopsy device 100, and the screw 30 and the peripheral wall 40 are effective to prevent the sampled cells from being scattered around in radial directions of the biopsy device 100. The living body is therefore protected against complications due to dissemination of malignant cells, for example.

The first screw cutter 31 peels cells off the living body when the screw 30 is rotated counterclockwise as viewed in front elevation in FIG. 3, whereas the second screw cutter 32 separates cells from the peeled-off cells as a specimen when the screw 30 is rotated clockwise.

Consequently, cells can easily be sampled as a specimen from the biological tissue B when the screw 30 is rotated in a direction opposite to the direction in which the screw 30 was rotated to peel cells off the living body.

The blade 41 of the peripheral wall 40 has its cutting edge, which serves as a leading edge, orientated in the same direction as the cutting edge of the first screw cutter 31 at the time the first screw cutter 31 is rotated to peel cells off the living body. For peeling cells off the living body, the first screw cutter 31 severs cells of the living body in the vicinity thereof into a group of cells on the distal side of the first screw cutter 31 and a group of cells on the proximal side thereof, and peels the cells on the proximal side off the living body, and the blade 41 divides the cells in the vicinity thereof into a group of cells positioned radially inwardly of the blade 41 and a group of cells positioned radially outwardly of the blade 41, and peels the cells positioned radially inwardly of the blade 41 off the biological tissue B. It is possible to peel a relatively large amount of cells off the biological tissue B in a single biopsy, and to sample a specimen required for a conclusive diagnosis in as a relatively small number of biopsies.

The tubular barrel 60 is connected to the proximal end of the screw 30 and has the lumen 61 defined therein around the shaft 10 extending axially through the tubular barrel 60, the lumen 61 being held in fluid communication with the opening 50. When the specimen that has been introduced through the opening 50 into the lumen 61 and adhered to the shaft 10 is prevented from dropping off from the biopsy device 100 when the biopsy device 100 is rotated. Therefore, the amount of cells contained in the specimen is prevented from being reduced once it is sampled by the biopsy device 100. Furthermore, since the lumen 61 wherein the sampled specimen is placed is isolated from the surrounding living body by the tubular barrel 60, the living body is protected against complications due to dissemination of the specimen which may contain malignant cells, for example.

Although the preferred embodiment of the present disclosure has been described in detail above, it should be understood that various changes and modifications may be made thereto without departing from the scope of the appended claims.

In the above embodiment, the blade 41 of the peripheral wall 40 has its cutting edge serving as a leading edge at the time the screw 30 is rotated counterclockwise as viewed in front elevation in FIG. 3. However, the cutting edge of the blade 41 of the peripheral wall 40 may serve as a leading edge at the time the screw 30 is rotated clockwise as viewed in front elevation in FIG. 3, i.e., may be oriented in the same direction as the second screw cutter 32.

It should be understood by those skilled in the art that various modifications, combinations, sub-combinations and alterations may occur depending on design requirements and other factors insofar as they are within the scope of the appended claims or the equivalents thereof.

While illustrative and presently preferred embodiments of the present invention have been described in detail herein, it is to be understood that the inventive concepts may be otherwise variously embodied and employed without departing from the spirit and scope of the invention. The appended claims are intended to be construed to include such variations and equivalents.

What is claimed is:

1. A biopsy device comprising:
   an elongated shaft extending from a proximal end to a distal end along a longitudinal axis;
   a piercing spike configured to pierce a biological tissue, the piercing spike being disposed on the distal end of the elongated shaft;
   a screw disposed on the elongated shaft, the screw configured to guide a specimen sampled from the biological tissue from the distal end of the elongated shaft toward the proximal end thereof;
   a first screw cutter disposed on the screw configured to peel the specimen off the biological tissue, and disposed on a distal end of the screw;
   a second screw cutter configured to separate the specimen peeled off the biological tissue, and disposed on a proximal end of the screw, wherein the first screw cutter is spaced apart from the second screw cutter along the longitudinal axis of the elongated shaft; and
   a peripheral wall having a cutting edge extending from the first screw cutter to the second screw cutter, wherein the cutting edge is spaced radially outward from the elongated shaft and a portion of the screw;
   wherein the first screw cutter is configured to peel the specimen off the biological tissue while the piercing spike is piercing the biological tissue.

2. The biopsy device according to claim 1,
   wherein the peripheral wall extends continuously from the first screw cutter to the second screw cutter.

3. The biopsy device according to claim 1,
   wherein the first screw cutter, the second screw cutter, and the peripheral wall jointly define therebetween an opening receiving the specimen.

4. The biopsy device according to claim 1,
   wherein the first screw cutter is configured to peel the specimen off the biological tissue when the screw is rotated in a first direction about the longitudinal axis of the elongated shaft, and
   the second screw cutter is configured to separate the specimen from the biological tissue when the screw is rotated in a second direction opposite the first direction.

5. The biopsy device according to claim 1,
   wherein the cutting edge is configured to serve as a leading edge when the peripheral wall is rotated in a direction in which the second screw cutter peels the specimen off the biological tissue.

6. The biopsy device according to claim 3, further comprising
   a hollow tubular barrel extending along the longitudinal axis from the proximal end of the elongated shaft to a proximal end of the screw and having a lumen defined therein around the shaft extending axially through the hollow tubular barrel, the lumen being held in fluid communication with the opening.

7. The biopsy device according to claim 1,
   wherein the intersection of the peripheral wall and the first screw cutter form an angle of less than 120 degrees.

8. The biopsy device according to claim 1,
   wherein the cutting edge is configured to peel the specimen off the biological tissue while the piercing spike is piercing the biological tissue.

9. A biopsy device comprising:
   an elongated shaft extending from a proximal end to a distal end along a longitudinal axis;
   a piercing spike configured to pierce a biological tissue, the piercing spike being disposed on the distal end of the elongated shaft;
   a screw disposed on the elongated shaft, the screw configured to guide a specimen sampled from the biological tissue from the distal end of the elongated shaft toward the proximal end of the elongated shaft;
   a first screw cutter disposed on the screw, configured to peel the specimen off the biological tissue;
   a second screw cutter configured to separate the specimen peeled off the biological tissue, and disposed on a proximal end of the screw, wherein the first screw cutter is spaced apart from the second screw cutter along the longitudinal axis of the elongated shaft; and
   a peripheral wall having a cutting edge extending continuously from the first screw cutter to the second screw cutter, wherein the cutting edge is spaced radially outward from the elongated shaft and covering a portion of the screw;
   wherein the cutting edge is configured to peel the specimen off the biological tissue while the piercing spike is piercing the biological tissue; and
   wherein the first screw cutter, the second screw cutter, and the peripheral wall jointly define therebetween an opening receiving the specimen.

10. A biopsy device comprising:
    an elongated shaft extending from a proximal end to a distal end along a longitudinal axis;
    a piercing spike configured to pierce a biological tissue, the piercing spike being disposed on a longitudinally distal end of the elongated shaft;
    a first screw cutter extending radially from the elongated shaft and a second screw cutter extending radially from the elongated shaft, wherein the first screw cutter and the second screw cutter are spaced longitudinally along the longitudinal axis of the elongated shaft;
    a peripheral wall having a blade portion extending from the first screw cutter to the second screw cutter, wherein the blade portion is spaced radially outward from the elongated shaft and a portion of the screw; and
    wherein the first screw cutter, second screw cutter and peripheral wall define an opening configured for a specimen to pass through.

11. The biopsy device according to claim 10,
    wherein a screw is disposed on the elongated shaft, the screw configured to guide a specimen from the longitudinally distal end of the elongated shaft toward a longitudinally proximal end thereof.

12. The biopsy device according to claim 10, wherein the opening is further defined by the screw.

* * * * *